United States Patent
Martin et al.

[11] Patent Number: 5,945,094
[45] Date of Patent: Aug. 31, 1999

[54] DISPOSABLE PLUG-IN DISPENSER FOR USE WITH AIR FRESHENER AND THE LIKE

[75] Inventors: John Martin, Caledonia; Mark E. Wefler, Mount Pleasant, both of Wis.

[73] Assignee: S. C. Johnson & Son, Inc., Racine, Wis.

[21] Appl. No.: 08/834,071

[22] Filed: Apr. 14, 1997

[51] Int. Cl.⁶ .................................................. A61L 9/00
[52] U.S. Cl. .................... 424/76.1; 424/400; 424/405; 239/44; 239/45; 239/50; 219/392; 392/390
[58] Field of Search .................. 392/390–395; 219/392; 239/44, 45, 50; 424/405, 76.1

[56] References Cited

U.S. PATENT DOCUMENTS

| | | | |
|---|---|---|---|
| 1,994,932 | 3/1935 | Vidal | 99/18 |
| 2,597,195 | 5/1952 | Smith | 21/119 |
| 2,611,068 | 9/1952 | Wellens | 219/19 |
| 2,802,695 | 8/1957 | Johnson | 299/24 |
| 2,804,291 | 8/1957 | Hard af Segerstad | 261/99 |
| 3,067,310 | 12/1962 | Walz et al. | 219/19 |
| 3,266,661 | 8/1966 | Dates | 220/64 |
| 3,288,556 | 11/1966 | Weber | 21/120 |
| 3,431,393 | 3/1969 | Katsuda | 219/274 |
| 3,482,929 | 12/1969 | Gentil | 21/53 |
| 3,550,853 | 12/1970 | Gray | 239/44 |
| 3,633,881 | 1/1972 | Yurdin | 261/24 |
| 4,020,321 | 4/1977 | Oswald | 219/271 |
| 4,037,352 | 7/1977 | Hennart et al. | 43/127 |
| 4,228,124 | 10/1980 | Kashihara et al. | 422/36 |
| 4,286,754 | 9/1981 | Jones | 239/6 |
| 4,314,915 | 2/1982 | Wiegers et al. | 252/522 |
| 4,411,829 | 10/1983 | Schulte-Elte et al. | 252/522 |
| 4,413,779 | 11/1983 | Santini | 239/45 |
| 4,434,306 | 2/1984 | Kobayashi et al. | 568/820 |
| 4,454,987 | 6/1984 | Mitchell | 239/6 |
| 4,631,387 | 12/1986 | Glucksman | 219/272 |
| 4,675,504 | 6/1987 | Suhajda | 219/272 |
| 4,849,255 | 7/1989 | Grise et al. | 427/122 |
| 4,849,606 | 7/1989 | Martens et al. | 219/271 |
| 4,857,384 | 8/1989 | Mio et al. | 428/164 |
| 4,912,306 | 3/1990 | Grise et al. | 219/549 |
| 4,913,350 | 4/1990 | Purzycki | 239/44 |
| 4,935,156 | 6/1990 | van Konynenburg et al. | 219/553 |
| 4,968,487 | 11/1990 | Yamamoto et al. | 422/125 |
| 5,000,383 | 3/1991 | van der Heijden | 239/47 |
| 5,014,338 | 5/1991 | Gluckman | 392/405 |
| 5,038,394 | 8/1991 | Hasegawa et al. | 392/395 |
| 5,106,540 | 4/1992 | Barma et al. | 252/511 |
| 5,111,477 | 5/1992 | Muderlak | 392/390 |
| 5,234,162 | 8/1993 | Sullivan | 239/56 |
| 5,242,111 | 9/1993 | Nakoneczny et al. | 239/47 |

(List continued on next page.)

FOREIGN PATENT DOCUMENTS

| | | |
|---|---|---|
| 0 689 766 | 1/1996 | European Pat. Off. . |
| 2 432 837 | 3/1980 | France . |
| 2741807 | 6/1997 | France . |
| 36 09 511 | 10/1986 | Germany . |
| 41 31 613 | 3/1993 | Germany . |
| 44 46 413 | 6/1996 | Germany . |
| 2 275 608 | 9/1994 | United Kingdom . |
| 94/15650 | 7/1994 | WIPO . |
| 9415650 | 7/1994 | WIPO . |
| 96/33605 | 10/1996 | WIPO . |

OTHER PUBLICATIONS

JGRAF et al. abstract of WPIDS #89–286469 of DE 3908493 Sep. 1989.

*Primary Examiner*—Neil S. Levy

[57] ABSTRACT

This invention provides a disposable air freshener dispenser device which is adapted for engagement and support by a wall electrical outlet. The dispenser device consists of a cartridge which has a sealed content of liquid air freshener medium, and an absorbent matrix which can be exposed for wicking of air freshener into the atmosphere. An electrical-resistance type heater module is detachably secured and positioned proximate to the exposed absorbent matrix section for promotion of the wicking action.

14 Claims, 2 Drawing Sheets

U.S. PATENT DOCUMENTS

| | | | |
|---|---|---|---|
| 5,290,546 | 3/1994 | Hasegawa et al. | 424/76.2 |
| 5,364,027 | 11/1994 | Kuhn | 239/44 |
| 5,382,384 | 1/1995 | Baigrie et al. | 252/511 |
| 5,402,517 | 3/1995 | Gillett et al. | 392/386 |
| 5,415,934 | 5/1995 | Mori | 428/408 |
| 5,521,357 | 5/1996 | Lock et al. | 219/543 |
| 5,522,008 | 5/1996 | Bernard | 392/392 |
| 5,556,192 | 9/1996 | Wang | 362/276 |
| 5,574,821 | 11/1996 | Babasade | 392/392 |
| 5,602,958 | 2/1997 | Vergnes | 392/395 |
| 5,647,052 | 7/1997 | Patel et al. | 392/390 |
| 5,647,053 | 7/1997 | Schroeder et al. | 392/390 |

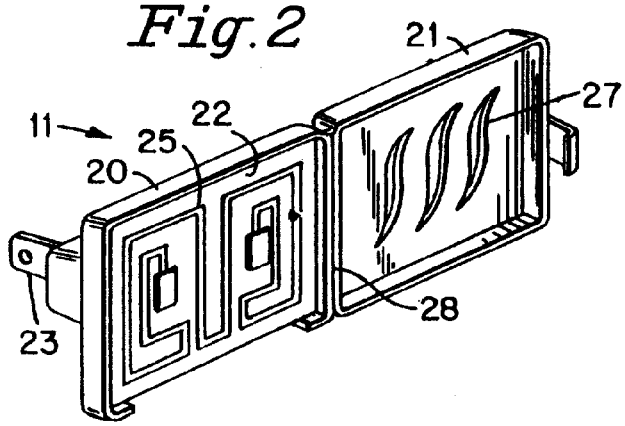
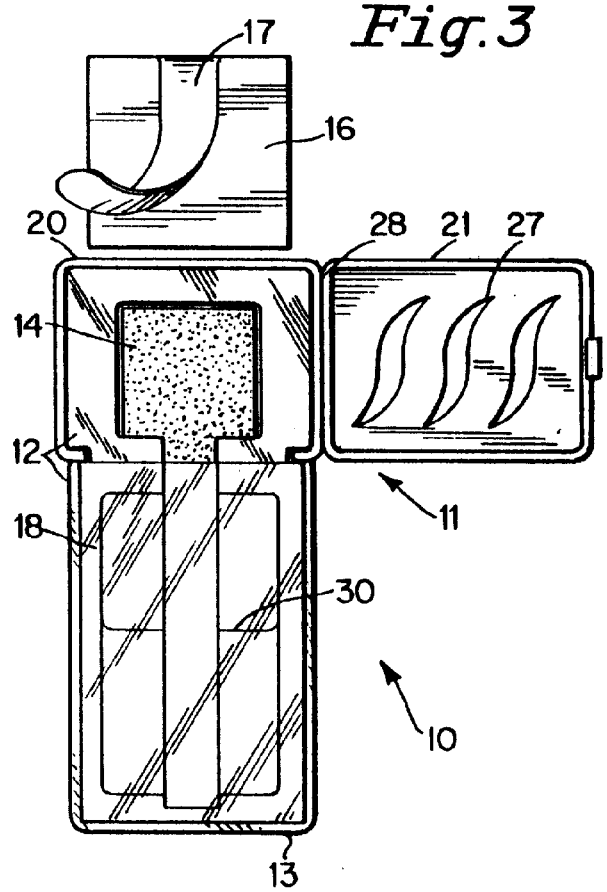
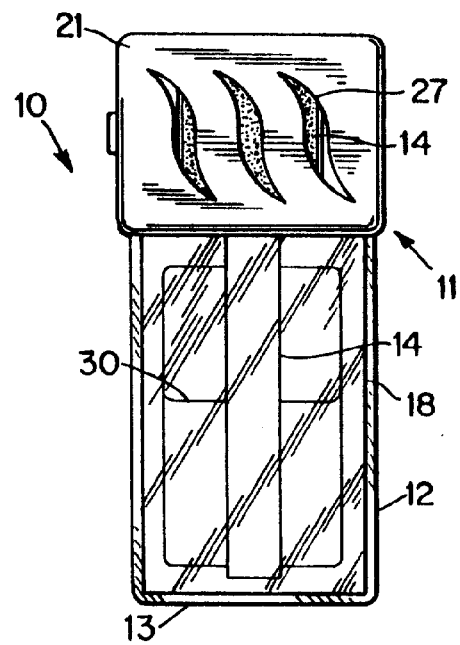
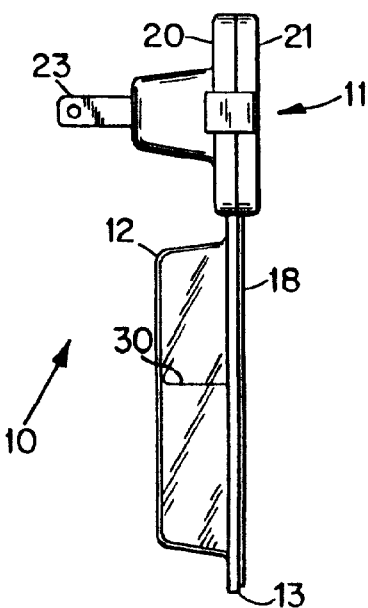

5,945,094

DISPOSABLE PLUG-IN DISPENSER FOR USE WITH AIR FRESHENER AND THE LIKE

BACKGROUND OF THE INVENTION

This invention generally relates to dispensers of vaporizable media. More specifically, this invention relates to a device for dispensing a fragrance or deodorant in the form of a vapor for air freshening in an enclosed environment.

The need for effectively combating airborne malodors in homes and enclosed public buildings, by odor masking or destruction, is well established. Various kinds of vapor-dispensing devices have been employed for this purpose. The most common of such devices is the aerosol container which propels minute droplets of an air freshener composition into the air. Another common type of dispensing device is a dish containing or supporting a body of gelatinous matter which when it dries and shrinks releases a vaporized air-treating composition into the atmosphere. Other products such as deodorant blocks are also used for dispensing air-treating vapors into the atmosphere by evaporation. Another group of vapor-dispensing devices utilizes a carrier material such as paperboard impregnated or coated with a vaporizable composition.

A number of recent developments include a liquid air-treating composition in an enclosure, all or part of which is formed of a polymeric film through which the air-treating composition can migrate to be released as a vapor at an outer surface. Use of this type of permeable polymeric membrane controls the dispensing of air-treating vapors and tends to eliminate great variations in the rate of dispensing over the life of the product. Wicking devices are well known for dispensing volatile liquids into the atmosphere, such as fragrance, deodorant, disinfectant or insecticide active agent.

A typical wicking device utilizes a combination of a wick and emanating region to dispense a volatile liquid from a liquid reservoir. Wicking devices are described in U.S. Pat. Nos. 1,994,932; 2,597,195; 2,802,695; 2,804,291; 3,550,853; 4,286,754; 4,413,779; 4,454,987; 4,913,350; and 5,000,383; incorporated by reference.

Of special interest with respect to the present invention are wicking dispenser devices in which the wicking action is promoted by a heat source. This type of wicking device is described in U.S. Pat. Nos. 3,288,556; 3,431,393; 3,482,929; 3,633,881; 4,020,321; 4,968,487; 5,038,394; 5,290,546; and 5,364,027; incorporated by reference.

Some air freshener dispensers are expensive to manufacture. Other air freshener dispensers are inexpensive to produce, but tend to have inferior construction and functionality.

There remains a need for a well-constructed air freshener dispenser device which can be mass-produced economically and which can deliver a vapor medium at a controlled uniform rate over an extended period of time.

Accordingly, it is an object of this invention to provide an improved air freshener dispenser device for delivering an odorant and/or deodorant vapor in an enclosed environment.

It is another object of this invention to provide an air freshener dispenser device with a primary structure which is a plastic assembly that can be produced economically by a thermoforming means.

It is another object of this invention to provide a disposable air freshener dispenser device which has an interactive combination of electrical resistance heater module and air freshener cartridge unit.

It is a further object of this invention to provide an air freshener cartridge for utility in a heat-activated air freshener dispenser device, wherein the cartridge has an internal air freshener reservoir in contact with a wicking means.

Other objects and advantages of the present invention shall become apparent from the accompanying description and drawings.

SUMMARY OF THE INVENTION

One or more objects of the present invention are accomplished by the provision of a disposable air freshener dispenser device which is adapted for engagement and support by a wall electrical outlet, and which is an assembly of structural units comprising:

(1) a cartridge which comprises (a) a thermoplastic tray having side walls with an upper edge flange which forms a peripheral margin around the open space of the tray, wherein the flange has an elongated extension from one wall, and the surface of the elongated flange extension has a shallow flat recess extending from the wall edge, (b) a thin emanating absorbent matrix with an upper section which fits within the flange flat recess, and with a lower section which extends across the open space of the tray to the opposite wall edge, (c) a volatile liquid air freshener medium which is contained within the tray interior, (d) a first vapor-impermeable membrane which covers the open space of the tray and the lower section of the absorbent matrix, and which is bonded to the tray peripheral margin and forms a sealed air freshener reservoir enclosure within the tray interior, and (e) a peelable second vapor-impermeable membrane which covers the upper section of the absorbent matrix; and (2) an electrical-resistance type heating means which is detachably secured and positioned proximate to the back surface of the tray elongated flange extension and the upper section of the absorbent matrix for promotion of air freshener wicking into the atmosphere, wherein the heating means comprises (a) a molded plastic electrical plug housing with a flat front surface and two inlet openings within the plug housing, (b) a detachable thin panel section which is juxtapositioned on the flat front surface of the plug housing, wherein the panel section comprises an electrical-resistance heater module, and has two apertures corresponding in position to the inlet openings within the plug housing, and (c) a pair of metal prongs which are positioned within the apertures of the panel section and the inlet openings of the plug housing, and which extend rearwardly from the plug housing for engagement with a wall electrical outlet, and said prongs are adapted to conduct electric current to the electrical-resistance heater module.

In another embodiment this invention provides a disposable air freshener dispenser device which is adapted for engagement and support by a wall electrical outlet, and which prior to assembly is an aggregate of conformational structural units comprising:

(1) cartridge components which comprise (a) a thermoplastic tray having side walls with an upper edge flange which forms a peripheral margin around the open space of the tray, wherein the flange has an elongated extension from one wall, and the surface of the elongated flange extension has a shallow flat recess extending from the wall edge, (b) a thin emanating absorbent matrix which fits within the flange flat recess, and has a lower section extendable across the open space of the tray to the opposite wall edge, and (c) a vapor-impermeable membrane which is bondable to the tray peripheral margin to form a sealed air freshener reservoir enclosure within the tray interior; and (2) plug-in electrical-resistance type heating components which comprise (a) a molded plastic electrical plug housing with a flat front surface and two inlet openings within the plug housing, (b) a thin panel section which comprises an electrical-resistance heater module, and has two apertures with position correspondence to the inlet openings within the plug housing, and (c) a pair of metal prongs for positioning within the apertures of the panel section and the inlet openings of the plug housing, wherein said prongs are adapted to conduct electric current to the electrical-resistance heater module in the assembled dispenser device having a reservoir content of liquid air freshener medium.

DESCRIPTION OF THE DRAWINGS

FIG. 2 is a perspective front view of an invention device plug-in electrical-resistance heater module.

FIG. 3 is an elevational front view of an invention disposable air freshener dispenser device after removal of a peelable vapor-impermeable membrane.

FIG. 4 is an elevational front view of a FIG. 3 invention dispenser device with a vented cover in a closed position.

FIG. 5 is an elevational side view of a FIG. 4 invention dispenser device with rearwardly extended metal prongs, and a reservoir content of liquid air freshener medium.

Figure 1:
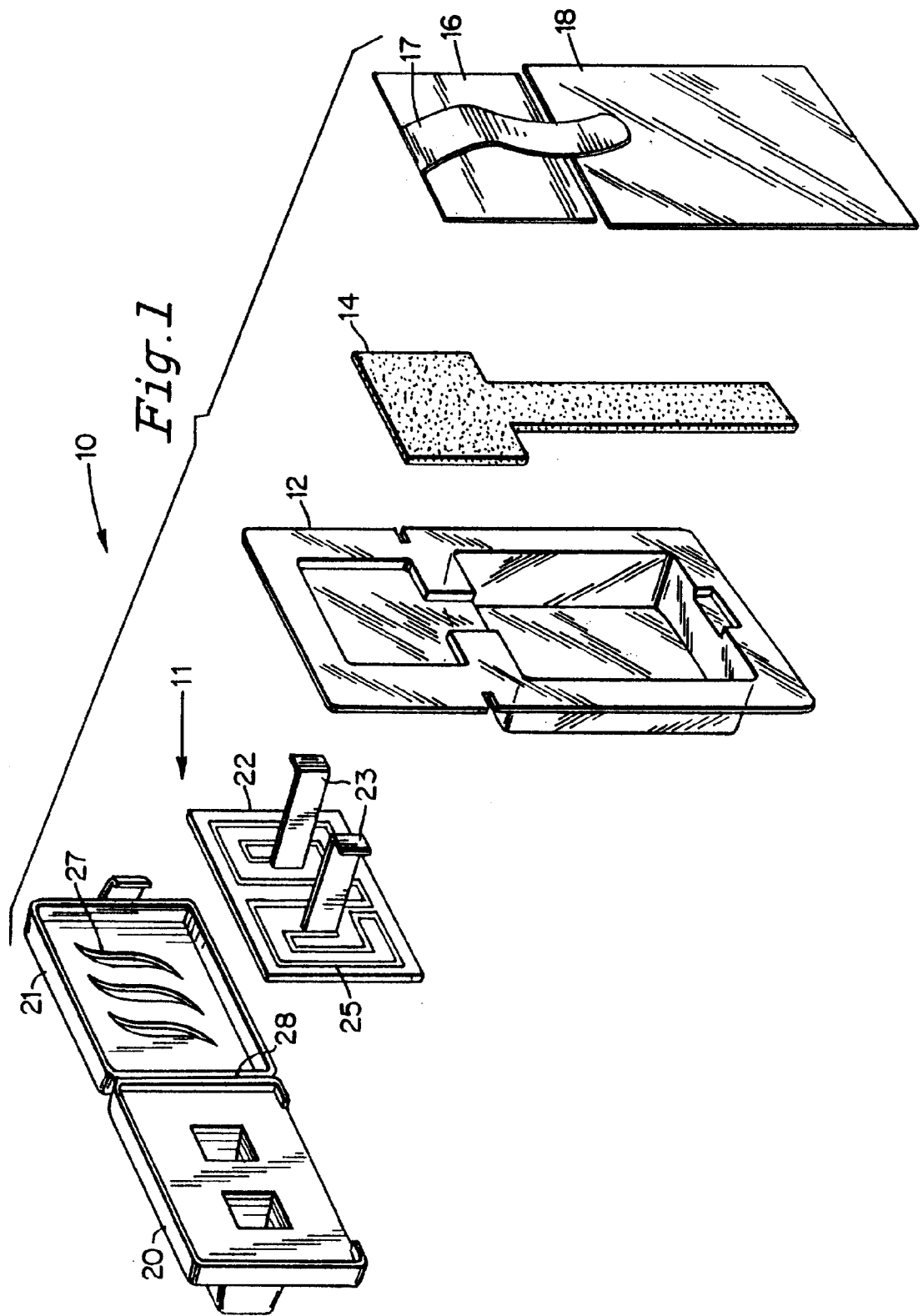
FIG. 1 is a composite perspective view of an invention air freshener dispenser device.

The device 10 includes a heater module 11 and a cartridge 12 in which the liquid medium will be contained.

The heater module 11 includes a panel section 22 on which is a printed electrical-resistance heating pattern 25. Electrically conductive prongs 23 can be inserted through a pair of apertures in the panel section 22 so as to engage the printed electrical-resistance heating pattern 25. An electrical plug housing 20 is provided for containing the panel section 22, and includes a pair of corresponding openings out through which the prongs 23 can extend.

The cartridge 12 includes a tray 12a, in which is formed an interior reservoir 12b and a shallow recess 12c. A flange 13 extends around the perimeter of the tray. A secondary recess 12d can be formed in the flange 13b opposite the recess 12c.

The cartridge also includes an absorbent matrix 14, which fits within the shallow recess 12c and extends into the reservoir 12b of the tray 12a. It is preferred that the absorbent matrix extend completely across the reservoir 12b into the secondary recess 12d. When the cartridge 12 is assembled, the reservoir 12b contains the liquid medium, and vapor-impermeable membranes 16, 18 seal the absorbent matrix 14 and the liquid medium within the tray 12a.

When the cartridge 12 and the heating module 11 are assembled together, the back surface of the shallow recess 12c of the tray 12a is positioned facing the printed electrical-resistance heating pattern 25. Thus, the portion of the absorbent matrix 14 sitting in the shallow recess 12c is held in thermal communication with the printed electrical-resistance heating pattern 25. Prior to use, the vapor-impermeable membrane 16 can be removed to expose the portion of the absorbent matrix 14 sitting in the shallow recess 12c.

DESCRIPTION OF THE PREFERRED EMBODIMENTS

FIG. 1 illustrates an exploded view of present invention air freshener dispenser device 10 without a liquid air freshener medium content.

In assembled form, air freshener dispenser device 10 is plugged into a wall electrical outlet by means of twin prongs 23 of heater module 11. Electric current is conducted by twin prongs 23 to printed electrical-resistance heating pattern 25 for promotion of liquid air freshener wicking out of the interior reservoir of cartridge 12 by absorbent matrix 14 after removal of peelable vapor-impermeable membrane 16.

FIG. 2 is a perspective front view of plug-in electrical-resistance heater module 11 in assembled form. Vented cover 21 is attached to electrical plug housing 20 by flexible hinge 28. As illustrated, electrical plug housing 20 and vented cover 21 together constitute a single unitary plastic structure formed by molding means from a thermoset polymer such as phenol-formaldehyde resin, epoxy resin, polyphenylene sulfide, polyphenylene oxide, polycarbonate, polyimide, polybenzimidazole, and the like, or a thermoplastic polymer such as polyethylene, polypropylene, polyamide, and the like.

Printed electrical-resistance heating pattern 25 on panel section 22 in FIG. 2 heater module 11 can be in the form of an electric-conductive ink or electric-conductive polymer with electrical-resistance properties for heat generation. Printed or thin film electrical-resistance heating elements are described in publications such as U.S. Pat. Nos. 3,067,310; 3,266,661; 4,849,255; 4,857,384; 4,912,306; 4,935,156; 5,106,540; 5,382,384; and 5,415,934; incorporated by reference. Panel section 22 can be a thermoset polymer such as Novalak resin, or a thermoplastic polymer such as polyvinyl chloride or polyvinyl acetate.

Cover 21 in FIG. 2 heater module 11 has at least one vent aperture 27 for release of air freshener vapor when invention air freshener dispenser device 10 is operational. Vent aperture 27 can have an adjustable open-close feature.

FIG. 3 is an elevational front view of invention air freshener dispenser device 10 after removal of peelable vapor-impermeable membrane 16, which can be a thin flexible material such as aluminum foil or nylon film. Tab section 17 facilitates the removal of membrane 16, for exposure of the upper emanating surface of absorbent matrix 14.

As illustrated in FIG. 3, after removal of vapor-impermeable membrane 16, liquid air freshener medium 30 is wicked by capillary action up absorbent matrix 14 out of the interior reservoir of cartridge 12, and is vaporized into the atmosphere. Vapor-impermeable membrane 18 is bonded to flange 13 to form a sealed air freshener reservoir enclosure in cartridge 12. Membrane 18 can be formed of different or the same material as membrane 16. Preferably, membrane 18 is translucent or transparent for viewing the level of air freshener 30 in cartridge 12. In another embodiment, membrane 16 and membrane 18 are taken together in the form of a single thin film, which has a peelable area for exposure of the upper section of emanating absorbent matrix 14 to allow air freshener wicking into the atmosphere.

FIG. 4 is an elevational front view of FIG. 3 invention dispenser device 10 with vented cover 21 in a closed position. Typically cartridge 12 is a translucent or transparent structure which is injection or thermoform molded from a polymer such as polyethylene, polypropylene, polystyrene, polyvinyl chloride, polyvinyl acetate, polyamide, polymethacrylate, and the like.

FIG. 5 is an elevational side view of FIG. 4 invention dispenser device 10 which illustrates the rearward positioning of brass prongs 23 for accessing a wall electrical outlet.

Cartridge 12 of invention dispenser device 10 as illustrated in FIGS. 3–5 typically has rectangular flange periphery dimensions between about 1–3 inches in width and 2–6 inches in length. The tray reservoir depth optionally can vary between about 0.2–0.6 inches.

Absorbent matrix 14 in FIGS. 3–5 can be an organic or inorganic liquid-permeable structure, such as a porous thermoplastic, thermoset, cellulosic or ceramic composition. The dimensions of absorbent matrix 14 are adapted to frictionally secure the structure within the conformational recesses provided in flange 13 of cartridge 12. Absorbent matrix 14 also can be in the form of a fibrous aggregate or a grooved nonporous strip. A variety of wick compositions and structures suitable for air freshener dispenser devices are described in U.S. Pat. Nos. 3,431,393; 3,482,929; 3,633,881; 4,020,321, 4,968,487; 5,038,394; and 5,290,546; incorporated by reference.

Air freshener medium 30 in FIGS. 3–5 can be any air treating material which can be wicked up absorbent matrix 14 by capillary action, and dispersed into the atmosphere in vapor form. Typically air freshener medium 30 is a fragrance or a deodorant formulation in liquid form.

Air freshener medium 30 preferably is a liquid fragrance comprising one or more volatile organic compounds which are available from perfumery suppliers such as Firmenich Inc., Takasago Inc., Noville Inc., Quest Co., and Givaudan-Roure Corp.

Most conventional fragrance materials are volatile essential oils. The fragrance can be a synthetically formed material, or a naturally derived oil such as oil of Bergamot, Bitter Orange, Lemon, Mandarin, Caraway, Cedar Leaf, Clove Leaf, Cedar Wood, Geranium, Lavender, Orange, Origanum, Petitgrain, White Cedar, Patchouli, Lavandin, Neroli, Rose absolute, and the like.

A wide variety of chemicals are known for perfumery, such as aldehydes, ketones, esters, alcohols, terpenes, and the like. A fragrance can be relatively simple in composition, or can be a complex mixture of natural and synthetic chemical components.

A typical scented oil can comprise woody/earthy bases containing exotic constituents such as sandalwood oil, civet, patchouli oil, and the like. A scented oil can have a light floral fragrance, such as rose extract or violet extract. Scented oil also can be formulated to provide desirable fruity odors, such as lime, lemon or orange.

Synthetic types of fragrance compositions either alone or in combination with natural oils are described in U.S. Pat. Nos. 4,314,915; 4,411,829; and 4,434,306; incorporated herein by reference. Other artificial liquid fragrances include geraniol, geranyl acetate, eugenol, isoeugenol, linalool, linalyl acetate, phenethyl alcohol, methyl ethyl ketone, methylionone, isobornyl acetate, and the like.

Air freshener medium 30 also can be a liquid formulation containing a volatile pesticide such as p-dichlorobenzene, or a therapeutic agent such as menthol.

Air freshener dispenser device 10 preferably is constructed of transparent or translucent materials, such that air freshener medium 30 is visible during usage for an indication of the liquid level in the interior reservoir of cartridge 12.

A present invention air freshener dispenser device can be produced in high volume from relatively inexpensive plastic materials. After usage, the device qualifies for disposal as a non-hazardous solid waste.

What is claimed is:

1. A disposable dispenser device for engagement and support by a wall electrical outlet, and which is an assembly of structural units, said device comprising:

a cartridge which comprises
  (a) a thermoplastic tray having a reservoir and a shallow recess, the reservoir and the shallow recess being contiguous and depressed in one side of the tray,
  (b) a volatile liquid medium which is contained within the reservoir,
  (c) an emanating absorbent matrix having a first section, disposed within the reservoir so as to be submersed in the liquid medium, and a second section, extending out of the liquid medium, and disposed within the shallow recess,
  (d) a first vapor-impermeable membrane bonded to the one side of the tray to cover the reservoir so as to encase the liquid medium and the first section of the absorbent matrix within the reservoir, and
  (e) a removable second vapor-impermeable membrane which covers the shallow recess so as to encase the second section of the absorbent matrix within the recess; and
an electrical-resistance heating module to which the cartridge is detachably securable, wherein the heating module comprises
  (a) a panel on which are formed an electrical-resistance heater and two apertures,
  (b) a pair of metal prongs which are positioned within the apertures of the panel and electrically engaged to the electrical-resistance heater, and
  (c) a plastic electrical plug housing to which the panel and the cartridge are detachably securable so that, when the panel and the cartridge are secured to the plug housing, the second section of the absorbent matrix within the shallow recess of the tray is held in thermal communication with the electrical-resistance heater of the panel, and the metal prongs extend from the housing for engagement with the wall electrical outlet to conduct electrical current to the electrical-resistance heater to promote liquid-medium wicking into the atmosphere.

2. A dispenser device in accordance with claim 1, wherein the cartridge thermoplastic tray is a molded polyvinyl structure with transparency, and the liquid medium in the tray reservoir is visible when the dispenser device is engaged with the wall electrical outlet.

3. A dispenser device in accordance with claim 1, wherein the absorbent matrix is a porous wick structure formed of a material selected from the group consisting of thermoplastic, thermoset, cellulosic and ceramic compositions.

4. A dispenser device in accordance with claim 1, wherein the liquid medium is a fragrance formulation.

5. A dispenser device in accordance with claim 1, wherein the first and second vapor-impermeable membranes are formed of a material selected from aluminum foil and nylon film.

6. A dispenser device in accordance with claim 1, wherein the first and second vapor-impermeable membranes taken together constitute a single thin film, and the second vapor-impermeable membrane is a peelable section of the single thin film that is removable for exposure of the second section of the emanating absorbent matrix for liquid medium wicking.

7. A dispenser device in accordance with claim 1, wherein the electrical plug housing is a structure molded from a material selected from the group consisting of thermoset and thermoplastic polymers.

8. A dispenser device in accordance with claim 1, wherein the electrical-resistance heater comprises a surface microfilm coating of electric-conductive polymer disposed on the panel.

9. A dispenser device in accordance with claim 1, further comprising a vented cover that selectively overlays and is detachably secured to the electrical plug housing so as to encase therebetween the electrical-resistance heater module and the second section of the absorbent matrix within the shallow flat recess of the tray.

10. A dispenser device in accordance with claim 9 wherein the electrical plug housing and the vented cover are integrally molded as a single plastic unit, and the vented cover is attached by a flexible hinge means to one side of said electrical plug housing.

11. A disposable dispenser device for engagement and support by a wall electrical outlet, and which, prior to assembly, is an aggregate of conformational structural units, said device comprising:

cartridge components, able to be assembled into a cartridge, which comprise
   (a) a thermoplastic tray having a reservoir, for containing a liquid medium, and a shallow recess, the reservoir and the shallow recess being contiguous and depressed in one side of the tray,
   (b) an emanating absorbent matrix having an upper section, which fits within the shallow recess, and a lower section, which extends into the reservoir, and
   (c) a vapor-impermeable membrane which is bondable to the one side of the tray to seal the reservoir and the shallow recess; and plug-in electrical-resistance heating components, able to be assembled into an electrical-resistance heating module, which comprise (a) a panel on which are formed an electrical-resistance heater and two apertures,
   (b) a pair of metal prongs provided for positioning within the apertures of the panel and for electrical engagement to the electrical-resistance heater in the assembled dispenser device, and
   (c) a plastic electrical plug housing to which the panel and the cartridge are detachably securable so that, when the panel and the cartridge are secured to the plug housing, the upper section of the absorbent matrix within the shallow recess of the tray is held in thermal communication with the electrical-resistance heater of the panel, and the metal prongs extend from the housing for engagement with the wall electrical outlet.

12. A dispenser device in accordance with claim 1, wherein the reservoir of the tray, with the liquid medium and the first section of the absorbent matrix encased therein, is spaced from the electrical-resistance heater module when the panel and the cartridge are secured to the housing.

13. A dispenser device in accordance with claim 1, wherein the first section of the absorbent matrix extends to a wall of the reservoir opposite the shallow recess.

14. A dispenser device in accordance with claim 1, wherein the tray further comprises a depression contiguous with the wall of the reservoir opposite the shallow recess, and the first section of the absorbent matrix extends into the depression.

* * * * *